United States Patent [19]

Sneer

[11] 4,081,908
[45] Apr. 4, 1978

[54] DENTAL IMPLANTS

[76] Inventor: Meer Sneer, 24 Merkas Baale Melacha St., Tel-Aviv, Israel

[21] Appl. No.: 703,379

[22] Filed: Jul. 8, 1976

[51] Int. Cl.² .......................................... A61C 13/00
[52] U.S. Cl. ................................................ 32/10 A
[58] Field of Search ..................................... 32/10 A

[56] References Cited

U.S. PATENT DOCUMENTS

| 3,827,145 | 8/1974 | Richards | 32/10 A |
| 3,905,107 | 9/1975 | Lenczycki | 32/10 A |
| 3,925,892 | 12/1975 | Juillet | 32/10 A |

*Primary Examiner*—Robert Peshock
*Attorney, Agent, or Firm*—Browdy and Neimark

[57] ABSTRACT

A dental implant comprising in combination a foundation member of V-shaped cross section, comprising two members connected at the spex of the V, the foundation member being adapted to be firmly connected with crown-support means, said foundation member being adapted to be inserted into the jaw so as to form a V-shaped structure or one having the shape of an inverted V. Preferably the foundation member plates have a plurality of holes.

6 Claims, 7 Drawing Figures

DENTAL IMPLANTS

BACKGROUND OF THE INVENTION

The present invention relates to novel dental implants. More specifically it relates to novel dental implants characterized by a very favorable ratio of surface area of the implanted foundation member of the implant to pressure exerted on the implant during chewing.

The ratio between applied pressure and the areas on which this is exerted is one of the most important parameters of dental implants. It determines to a large extent the success or failure of dental implants. The F/S index was determined by the inventor for natural teeth, and for various types of dental implants. The ratio F/S expresses the ratio of pressure per unit area (where the area is given in square millimeters), and the pressure in grams.

The F/S ratio of natural teeth varies between about 50 to 60. The F/S ratio of certain dental implants of the single blade type is about 2000. For other types of dental implants this ratio varies: screw type dental implants have a F/S ratio of 400 to 500; conus shaped implants have one of about 100.

BRIEF DESCRIPTION OF THE INVENTION

The novel implant comprises a base member which, in side view, has the form of a V or of an inverted V. The two members forming the V (or inverted V) are rectangular, or of similar shape, such as a shape with rounded edges, of curved shape etc.

The V-shaped structure (which applies both to the V and to the inverted V) can be a permanent structure, or it can be hinged at the apex. The dental implant is advantageously provided with shockabsorbing means. The implant can be made of any biologically acceptable material of adequate mechanical strength, such as metal, ceramic, vitreous carbon, plastic or the like. It can be provided with a porous surface layer, as described in U.S. Pat. No. 3,955,280.

The two members defining the V-shaped structure are advantageously provided with a plurality of holes, which make it possible for bone to grow into the space defined by this structure. The holes can be of different sizes, and generally a size of from 0.5 to 1.5 mm diameter is satisfactory.

The V-shaped foundation member is inserted into the jaw-bone (either as a V-shaped structure, with the apex of the V at the lowermost portion of the bone), or in the shape of an inverted-V. In both cases it is advantageous to resort to the two-stage method of implantation, as described and claimed by the inventor in U.S. Pat. No. 3,589,011. The dental implant comprises an upper member, which serves as crown-support or as support for other dental structures, and means are provided for firmly connecting the lower and the upper part of the implant.

It is possible to insert the implant in one stage, but generally the results thus obtained are inferior to those of the two-stage method, which allows adequate time for healing and for osteogenesis while the foundation member is not yet exposed to stresses due to chewing. After completion of this process, the upper part of the dental implant is attached. The dental implants of the present invention are characterized by a substantially larger surface in contact with the surrounding bone than used hitherto and thus the pressure per unit area is less, reducing substantially the danger of osteolysis and of rejection of the implant.

According to a preferred embodiment of the invention, the V-shaped structure is hinged, and shock-absorbing means are provided between the inner surface of the V-shaped structure and the member carrying the upper part of the implant.

Large teeth exert a pressure of about 50kg during chewing. Blade type implants exert this pressure on an effective area of only 20 to 30 mm$^2$, and this results in serious problems, such as osteolysis, degeneration of the bone etc., leading ultimately to a failure of the implant.

Contrasted with such blade implants, the effective supporting area of the novel inverted-V-shaped foundation member implants of the invention is much larger. The effective area is about 400 to 600 mm$^2$, and thus the pressure per unit area is about 50000/400–600 g/mm$^2$. Natural teeth have an effective area of about 400 mm$^2$, and the pressure is 50000/400 g/mm$^2$ = 125.

The foundation member can be made of any suitable material. Best results are obtained with a suitable physiologically acceptable plastic or metal. Good results were obtained with metal or plastic members of from about 0.5 to 1.0 mm thickness, bent at an angle of from 10 to about 30°, the size being about 10 mm height to about 20 to 35 mm width.

It is one of the more important advantages of the novel implant that there is practically no epithelization after the implantation of the first stage (of the foundation member).

According to yet a further embodiment of the invention the implant can be made of a foundation member which is V-shaped, carrying a bridging member on its upper part, said bridging member forming the support for the crown-support member. The inverted-V-foundation member straddles the mandibular nerve without contacting it, and even protects it from both sides.

With this embodiment, the V-shaped insert is introduced into the jaw bone, and left in place. This member is also provided with a plurality of holes, and during a certain period of time osteogenesis takes place and the bone growth into the inner space of the V-shaped foundation member. In this case the entire outer surface of the foundation member is in contact with the adjacent bone, and bears the pressure exerted on same during chewing. The pressure is further reduced by the provision of shock-absorbing means in said implant, preferably in the upper part of the crown support. Means can be provided for adjusting and varying at will the angle of the V-shaped member.

The provision of shock-absorbing means in the implant reduces the effective pressure exerted on the underlying bone by a factor of about 15 to 20 percent, the provision of a further shock absorber between the foundation member and the upper part further reduces the pressure on the bone.

If any unexpected complication arises, such as osteolysis, it is easy to remove the upper part of the implant, to close the mucosa and to let the bone recover. After such recovery the upper part is reinserted, and thus it is not necessary to resort to the complicated and unpleasant removal of the entire implant.

The novel implants have an index F/S as low as 60, and this is further reduced to an effective value of less than 50 by the provision of the shock absorbing means. Thus the novel implants have an F/S index which is even lower than that of natural teeth, and thus they exert a lesser strain on the jaw bone than natural teeth.

BRIEF DESCRIPTION OF THE DRAWINGS

The invention is illustrated with reference to the enclosed drawings in which.

DESCRIPTION OF THE PREFERRED EMBODIMENTS

Figure 1:
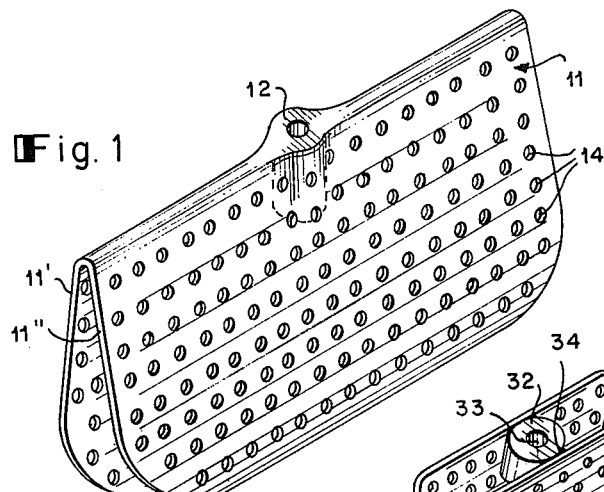
FIG. 1 is a schematical perspective view of a foundation member of an implant according to the invention.
Figure 2:
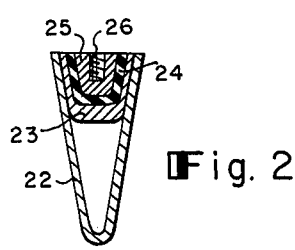
FIG. 2 is a schematical sectional side view of another foundation member.
Figure 4:
FIG. 4 is a schematical side view of an implant device embedded in the tissues of the jaw.
Figure 5:
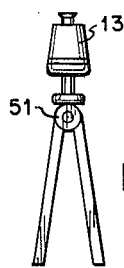
FIG. 5 is a side view of another implant device and FIG. 6 is yet another schematical side-view of an implant device according to the invention.

As shown in the FIGS. 1, 4 and 5, the implant device according to the invention comprises a foundation member 11 in the shape of an inverted V, comprising two substantially rectangular members 11' and 11", defining an angle of from about 10° to about 30°. At the middle of the upper edge there is provided a member 12 with a screw-bore adapted to receive the screw at the lower end of the crown support member 13. As shown in FIG. 1, the members 11' and 11" are preferably provided with rounded edges. These are preferably provided with a plurality of holes 14. As shown in FIG. 2, the foundation member 22 has a V shaped profile, and at the upper part of the V-shaped member there is fixedly attached a cup-shaped member 23, in which there is provided a shock-absorber comprising a cup-shaped member 24 made of a resilient material, inside which there is firmly bonded another insert, 25 provided with an internal screw-bore 26 adapted to support the crown support member.

Figure 3:
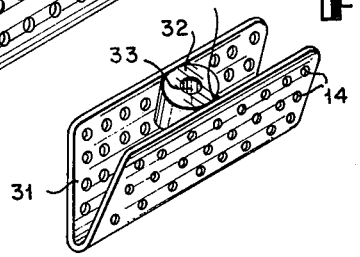
FIG. 3 is a perspective view of another foundation member of the implant device of the invention.

As shown in FIG. 3, the V-shaped member 31 is provided with a plurality of holes, 14, and at the upper part there is firmly attached to one of the sides of the V a cyclindrical member 32, provided with a screw-bore 33. On the other side of the insert, there is provided a resilient insert 34, which serves as shock-absorber.

As shown in FIG. 4, the assembled implant device comprises a foundation member 41, provided with a plurality of holes 42. This is provided with a firmly attached member 43, adapted to support the crown-support member 13, which comprises a neck-portion 44, a screw engaging the member 43, and an upper section 45 provided with a thin layer 46 of resilient material, firmly bonded to the part below and above it, which layer serves as effective shock absorber. The implantation in the tissue is illustrated.

Figure 6:
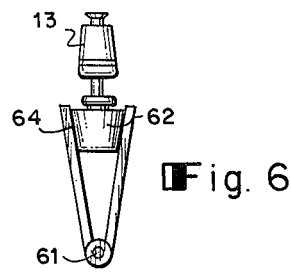

As shown in FIG. 5, the inverted V-shaped foundation member is provided with a hinge 51 which makes it possible to vary the angle at will. Such a hinge 61 is also provided in the implant device set out in FIG. 6. In this embodiment there is provided a cup-shaped member 62 bonded at the left-hand side to the inner wall of the V-shaped member 63, whereas at the right-hand side there is provided an inner layer 64 of resilient material.

Figure 7:
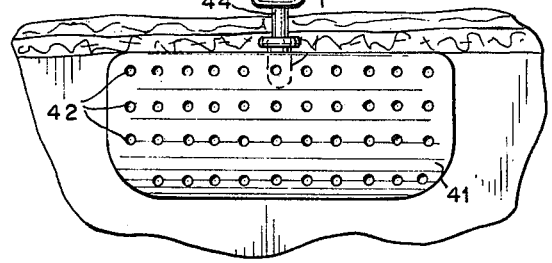
FIG. 7 is a schematical perspective view of another embodiment.
Figure 7:
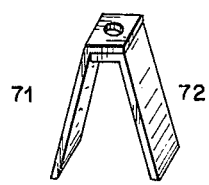

As shown in FIG. 7, the V-shaped implant may also be made from two members 71 and 72, firmly attached to each other so as to form a structure of the desired shape. When implanted, this structure advantageously straddles the mamdibular bone, which forms a firm support for same and which ensures a successful implant which will not be rejected during prolonged active use.

I claim:

1. A dental implant comprising in combination a foundation member of V-shaped cross section, comprising two members connected at the apex of the V;

said two members comprising plates of substantially rectangular shape, of about 10 mm. height and about 20–35 mm. width, forming an angle of 10° to 30° with each other;

the foundation member having crown-support connecting means provided with cup-shaped shock-absorbing means, said foundation member being adapted to be inserted in to the jaw.

2. A dental implant device according to claim 1 wherein the two plates forming the V-shaped structure are hinged.

3. A dental implant device according to claim 1 wherein the shock-absorbing means are provided between the inner part of the V and the crown-support member.

4. An implant as claimed in claim 1 wherein the F/S ratio of pressure per unit area is lower than 80.

5. A dental implant device according to claim 1 wherein the foundation member is made of metal, ceramic, plastic, vitreous carbon, optionally provided with a porous surface layer.

6. A dental implant device according to claim 1, wherein the crown-support connecting means is connected to one of said members at a point thereon opposite the apex.

* * * * *